United States Patent
Kuang et al.

(10) Patent No.: US 10,562,979 B1
(45) Date of Patent: Feb. 18, 2020

(54) HYBRIDOMA CELL LINE OF SECRETING MELOXICAM MONOCLONAL ANTIBODIES AND APPLICATION THEREOF

(71) Applicant: JIANGNAN UNIVERSITY, Wuxi, Jiangsu (CN)

(72) Inventors: Hua Kuang, Jiangsu (CN); Chuanlai Xu, Jiangsu (CN); Lu Lin, Jiangsu (CN); Liguang Xu, Jiangsu (CN); Wei Ma, Jiangsu (CN); Liqiang Liu, Jiangsu (CN); Xiaoling Wu, Jiangsu (CN); Shanshan Song, Jiangsu (CN); Yongming Hu, Jiangsu (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/222,377

(22) Filed: Dec. 17, 2018

(30) Foreign Application Priority Data

Aug. 3, 2018 (CN) .......................... 2018 1 08758612

(51) Int. Cl.
| | | |
|---|---|---|
| C07K 16/44 | (2006.01) | |
| C12N 5/12 | (2006.01) | |
| G01N 33/94 | (2006.01) | |
| C07D 417/12 | (2006.01) | |
| G01N 33/487 | (2006.01) | |
| G01N 33/02 | (2006.01) | |

(52) U.S. Cl.
CPC ............ *C07K 16/44* (2013.01); *C07D 417/12* (2013.01); *C12N 5/12* (2013.01); *G01N 33/02* (2013.01); *G01N 33/48714* (2013.01); *G01N 33/94* (2013.01)

(58) Field of Classification Search
None
See application file for complete search history.

(56) References Cited

FOREIGN PATENT DOCUMENTS

| CN | 104825474 A | 8/2015 |
| CN | 107073010 A | 8/2017 |
| CN | 107723278 A * | 2/2018 |

* cited by examiner

*Primary Examiner* — Brian Gangle
(74) *Attorney, Agent, or Firm* — Enshan Hong; VLP Law Group LLP

(57) ABSTRACT

A hybridoma cell line of secreting meloxicam monoclonal antibodies with a preservation number of hybridoma cell line of CGMCC No. 14700 belongs to the field of food safety immunological detection. The. BALB/c mice are immunized through one time immunization with complete freund's adjuvant, three times of booster immunization with incomplete freund's adjuvant and one time of rush immunization with meroxicam complete antigen without adjuvant; the spleen cells from BALB/C mice immunized with high potency and low value of IC50 are fused with murine myeloma cells; and then the hybridoma cell line is obtained through indirect competitive ELISA screening and three sub-clones. The monoclonal antibody secreted by this cell line has good specificity and detection sensitivity to meloxicam (value of IC50 is 0.1 ng/ml), being suitable for detection of meroxicam in food.

2 Claims, 1 Drawing Sheet

Concentration of standard meroxicam(ng/Ml)

HYBRIDOMA CELL LINE OF SECRETING MELOXICAM MONOCLONAL ANTIBODIES AND APPLICATION THEREOF

CROSS-REFERENCES TO RELATED APPLICATIONS

This application claims priority from China Patent Application Serial Number 2018108758612, which was filed on Aug. 3, 2018, the entire content of which is incorporated herein as reference.

BACKGROUND OF THE INVENTION

1. Technical Field

The invention relates to the hybridoma cell line of secreting meloxicam monoclonal antibodies and application thereof, belongs to the technical field of food safety and immunological detection.

2. Background Art

Meloxicam is an enol-type non-steroidal anti-inflammatory drug that has anti-inflammatory, analgesic and anti-pyretic effects, and is mainly used to relieve symptoms of osteoarthritis, painful osteoarthritis, rheumatoid arthritis, and strong and rigid spondylitis. In the field of veterinary clinic, meloxicam has been used in cows and pets and other animals. It was reported that meloxicam was used for the treatment of dairy cow mastitis, postoperative pain in gilts, adjuvant treatment of gilts mastitis and lacte-free syndrome. On 26 Jul. 2016, the Australian bureau of pesticides and veterinary medicine (APVMA) issued bulletin no. 15, amending the maximum residue limit (MRLs) of meloxicam in food. According to the bulletin, the maximum residue limits of fattened sheep, kidney of sheep, liver of sheep and mutton were set as 0.01 mg/kg, 0.01 mg/kg, 0.01 mg/kg and 0.01 mg/kg respectively.

Therefore, it is of great significance and market value to establish a rapid and effective method for the detection of meloxicam content.

At present, the detection methods of meloxicam are mainly High Performance Liquid Chromatography (HPLC), Liquid chromatography-tandem mass spectrometry (LC-MS/MS), enzyme-linked immunosorbent, immunoaffinity chromatographic column and electrochemical sensor, etc. However, these methods are cumbersome, time-consuming and expensive, and cannot achieve rapid detection of a large number of samples. Therefore, it is of great significance to establish a rapid and simple detection method.

Enzyme-linked immunoassay (ELISA) is an extremely efficient, sensitive and rapid detection methods, which requires less purity and is easy to operate, being suitable for rapid detection of a large samples. However, the precondition for the detection of meloxicam by enzyme-linked immunosorbent assay is to obtain monoclonal antibodies with high specificity and sensitivity to meloxicam. Therefore, it is critical to find a method to prepare monoclonal antibodies with high specificity and sensitivity to meloxicam.

The inventors attempted to prepare the monoclonal antibody against meloxicam by means of hybrid tumor cells, however it was still needed further research and validation that how to prepare meroxicam haptens and meroxicam complete antigens, how to make mice immune, whether the prepared hybrid tumor cell line can secrete the monoclonal antibody of meloxicam and What the specificity and sensitivity of the meroxicam monoclonal antibody is.

SUMMARY OF THE INVENTION

The purpose of the present invention is to obtain a kind of hybridoma cell line of secreting meroxicam monoclonal antibodies. The monoclonal antibody secreted by this hybrid tumor cell line has good specificity and detection sensitivity to meloxicam (IC50 value is 0.1 ng/mL), which could be used to establish the immunological detection method of meloxicam, and to detect the residues of cloxicam in food.

The invention provides a hybrid tumor cell line that secretes the monoclonal antibody of meloxicam, which has been deposited with the general microbiological center of China General Microbiological Culture Collection Center (No. 3, Yard 1, West Beichen Road, Chaoyang District, Beijing, China) under Accession Number CGMCC No. 14700.

The present invention provides a preparation method for a hybrid tumor cell line that secretes meloxicam monoclonal antibody, and contains the following steps:

Step 1: The complete antigen of meloxicam was synthesized by the preparation of meloxicam hapten. The complete antigen of meloxicam was mixed with the equivalent oil agent, and then the emulsifier was added, and the incomplete freund's adjuvant was obtained after emulsification. Complete freund's adjuvant was obtained by adding *mycobacterium* into incomplete freund's adjuvant. The oil agent described above is paraffin oil or vegetable oil; the emulsifier described above is lanolin or leaf tween 80; the *mycobacterium* described above includes dead shoots Step 2: The obtained freund's adjuvant was injected into BALB/c mice for several times for immunization subcutaneously through the back. Complete freund's adjuvant is used for the first time for immunization, while incomplete freund's adjuvant is used to strengthen immunity.

Step 3: Blood samples were taken from the mice after the above immune process, and the serum immune titer and immunosuppressive ability were detected by indirect ELISA to select the mice with high serum meroxicam antibody content.

Step 4: The selected mice were subjected to one last booster immunization with Incomplete Freund's adjuvant, and then, the impact immunity is performed via intraperitoneal injection, using meroxicam complete antigen without freund's adjuvant.

Step 5: The spleen cells and myeloma cells of BALB/c mice after impact immunity are fused, and the fusion cells were cultured. The positive cell pores were detected by ic-ELISA, and the inhibitory effect of positive cell pores was determined by IC-ELISA. Subclones of positive cells with the best inhibition were performed by limited dilution method, and the hybrid tumor cell lines that could secrete the monoclonal antibody of meloxicam were screened out.

The molecular formula of meloxicam hapten in step 1 is as follows:

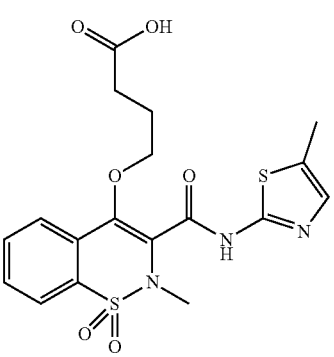 [SMILES: Cc1cnc(NC(=O)C2=C(OCCCC(=O)O)c3ccccc3S(=O)(=O)N2C)s1]

In an embodiment of the invention, the interval between the first immunization and the booster immunization in steps 2 and 4 is 28 days, the interval between the booster immunization is 21 days, and the interval between the booster immunization and the rush immunization is 21 days.

In an embodiment of the invention, the immune process in steps 2 and 4 comprises one time first immunization, three times booster immunization and one time rush immunization.

In an embodiment of the invention, the blood collection in step 3 is performed on the seventh day after the end of the third immune process.

In one embodiment of the invention, the cell fusion in step 5 is performed 3 days after the end of rush immunization.

In one embodiment of the present invention, the cell fusion in step 5 is performed by the PEG1500 method.

In one embodiment of the invention, the medium in step 5 is RPMI-1640.

In one embodiment of the invention, the time of subclones in step 5 is 3.

The present invention provides the above hybrid tumor cell line that secretes the monoclonal antibody of meloxicam or the application of the preparation method of the above hybrid tumor cell line that secretes the monoclonal antibody of meloxicam in the preparation of the monoclonal antibody of meloxicam.

The present invention provides a meroxicam hapten. and the molecular formula of the meroxicam hapten is as follows:

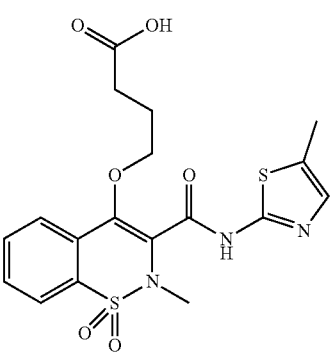 [SMILES: Cc1cnc(NC(=O)C2=C(OCCCC(=O)O)c3ccccc3S(=O)(=O)N2C)s1]

The invention provides a preparation method for the above meroxicam hapten, including the following steps:

Step 1: compound 1 was dissolved in methanol solution and MeONa was added for stirring to obtain mixture 1.

Step 2: the compound 2 was obtained through the mixture mentioned above was concentrated.

Step 3: compound 2 was dissolved in DMF and added Ethyl 4-bromobutyrate to stir to get mixture 2.

Step 4: mixture 2 was concentrated and purified to obtain compound 3.

Step 5: compound 3 was dissolved in the mixture of tetrahydrofuran and water, adjusting pH through adding lithium hydroxide of one hydrate and stir to get mixture 4.

Step 6: The aqueous solution layer of mixture 4 was extracted with ethylamine extract the aqueous solution, the organic layer was combined and washed, dried and concentrated to obtain meloxicam hapten.

The molecular formula of compound 1 is as follows:

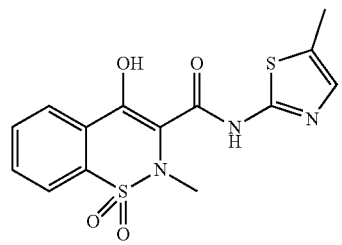 [SMILES: Cc1cnc(NC(=O)C2=C(O)c3ccccc3S(=O)(=O)N2C)s1]

The molecular formula of compound 2 is as follows:

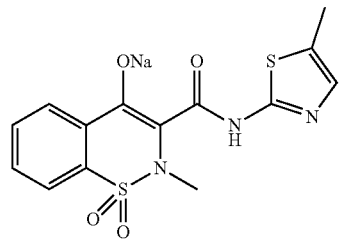

The molecular formula of the compound 3 is as follows:

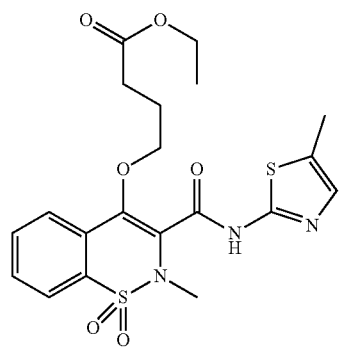 [SMILES: CCOC(=O)CCCOC1=C(C(=O)Nc2ncc(C)s2)N(C)S(=O)(=O)c2ccccc21]

The molecular formula of the meroxicam hapten is as follows:

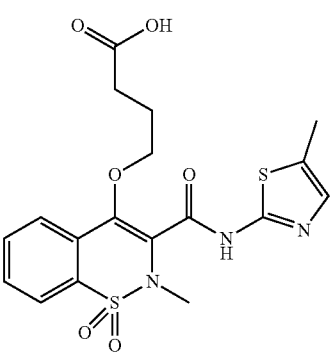 [SMILES: Cc1cnc(NC(=O)C2=C(OCCCC(=O)O)c3ccccc3S(=O)(=O)N2C)s1]

In a way of implementation of the invention, as described in step 1, 1 g of compound 1 was dissolved in 50 ml of methanol solution, and stirred at 157° C. for the night after adding 157 mg MeONa, and then the compound 1 was gotten.

In a way of implementation of the invention, as described in step 3, 1.20 g of compound 2 was dissolved 30 ml DMF, and added 1.20 mg 4-bromine ethyl butyrate stir at 80° C. for the night, and then the mixture 2 was gotten.

In one embodiment of the present invention, the step 4 is to concentrate the obtained mixture 2 and then purify it with a silica gel column to obtain compound 3.

In an embodiment of the invention, step 5 is to dissolve 800 mg compound 3 in a mixture of 3 mL tetrahydrofuran and 1 mL water, add 180 mg 1-hydrated lithium hydroxide, adjust pH to 4-6, and stir at room temperature overnight to get mixture 4.

In one embodiment of the invention, step 6 is to extract the aqueous solution layer with ethylamine from mixture 4, combine the organic layer, wash with salt water, dry with anhydrous sodium sulfate and concentrated to obtain meloxicam hapten.

The invention provides a meroxicam hapten or the preparation method of meroxicam hapten is used to prepare meroxicam complete antigen, a hybrid tumor cell line that secretes the monoclonal antibody of meloxicam or meroxicam monoclonal antibody.

The invention provides a meroxicam complete antigen which is obtained by the combination of meloxicam hapten and carrier protein KLH via EDC. The molecular formula of the meroxicam hapten is as follows:

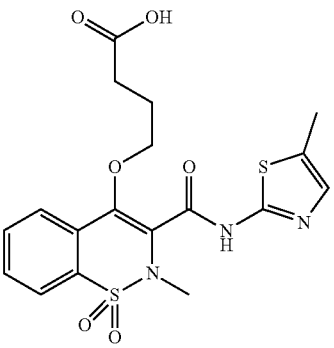 [SMILES: Cc1cnc(NC(=O)C2=C(OCCCC(=O)O)c3ccccc3S(=O)(=O)N2C)s1]

The invention provides a preparation method for the complete antigen of meloxicam, which the method is to dissolve meloxicam hapten (Melo), 1-ethylenediamine hydrochloride and n-hydroxysuccinylimide in anhydrous N,N-dimethylformamide, and obtain A1 solution. The B1 solution was obtained by dissolving the keyhole blood blue protein (KLH) into boric acid buffer solution. When A1 solution is added to B1 solution, the mixture is obtained. When the mixture is separated, complete antigen (Melo-KLH) is obtained.

The molecular formula of the meroxicam hapten is as follows:

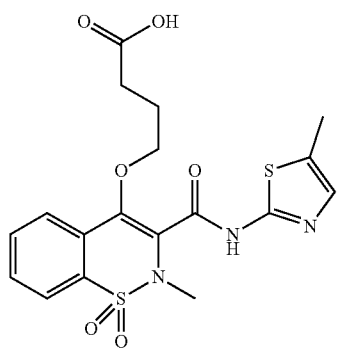 [SMILES: Cc1cnc(NC(=O)C2=C(OCCCC(=O)O)c3ccccc3S(=O)(=O)N2C)s1]

In one embodiment of the invention, the molar ratio of the meroxicam hapten (Melo) to the keyhole blood blue protein (KLH) is 1,500:1 or 3,000:1 or 4,500:1.

In one embodiment of the invention, the molar ratio of the meroxicam hapten (Melo) to the keyhole blood blue protein (KLH) is 1,500:1.

In one embodiment of the invention, the method is to dissolve 1.7 mg Melo 2.2 mg 1-ethylenediamine hydrochloride 1.4 mg N-hydroxysuccinylimide in 400 phenyl-anhydrous N,N-dimethylamine, and stir 6-8 h at room temperature to obtain A1 solution. 10 mg keyhole blood blue protein (KLH) was dissolved in 4 mL boric acid buffer solution, and B1 solution was obtained. At room temperature, A1 solution was added to B1 solution one drop at a time. Complete antigen (Melo-KLH) is obtained by separating complete antigen and uncoupled small molecule hapten (Melo) by dialysis.

The present invention provides a meloxicam coating antigen, which is characterized in that the meloxicam coating antigen is obtained by the combination of meloxicam hapten and carrier protein OVA via EDC method coupling.

The molecular formula of the meroxicam hapten is as follows:

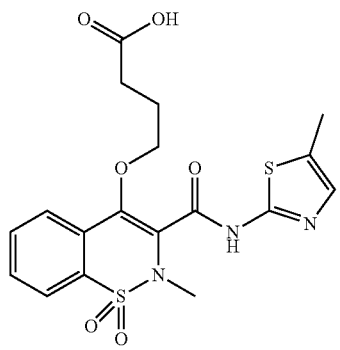 [SMILES: Cc1cnc(NC(=O)C2=C(OCCCC(=O)O)c3ccccc3S(=O)(=O)N2C)s1]

The invention provides a preparation method for the meloxicam coating antigen. The method is to dissolve meloxicam hapten (Melo), 1-ethylenediamine hydrochloride and n-hydroxysuccinylimide in anhydrous N, n-dimethylamine, and obtain A2 solution. The chicken egg albumin (OVA) was dissolved in boric acid buffer solution to obtain B2 solution. When A2 solution was added to B2 solution, mixed solution was obtained. The mixture was separated, then coating antigen (melo-ova) was obtained.

The molecular formula of the meroxicam hapten is as follows:

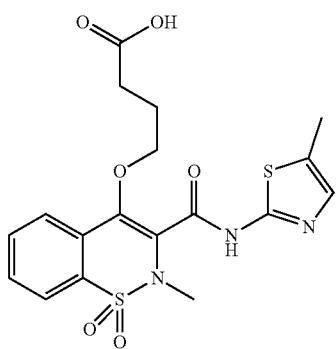 [SMILES: Cc1cnc(NC(=O)C2=C(OCCCC(=O)O)c3ccccc3S(=O)(=O)N2C)s1]

In one embodiment of the invention, the molar ratio of the meroxicam hapten (Melo) and the chicken egg albumin (OVA) is 30:1.

In one embodiment of the invention, the method is to dissolve 1.8 mg Melo 2.4 mg 1-ethylenediamine hydrochloride salt 1.45 mg N-hydroxysuccinylimide in 300 phenylanhydrous N,N-dimethylamine, and stir it back 6-8 h at room temperature to obtain A2 solution. 5 mg of chicken egg albumin (OVA) was dissolved in 2 mL boric acid buffer solution to obtain B2 solution. At room temperature, A2 solution was added to B2 solution, and mixed solution was obtained after overnight reaction at room temperature. Complete antigens, uncoupled small molecule haptens (Melo) and coating antigen (Melo-OVA) were separated by dialysis.

The invention provides the application of the above meroxicam complete antigen or the above meroxicam coating antigen in the preparation of the hybrid tumor cell line secreting meroxicam monoclonal antibody and meroxicam monoclonal antibody.

The present invention provides a monoclonal antibody of meroxicam, which is obtained by secretion of a hybrid tumor cell line with the preservation number CGMCC No. 14700.

The invention provides a preparation method of meroxicam monoclonal antibody, BALB/c mice were intraperitoneally injected with paraffin oil, and then intraperitoneally injected with hybrid tumor cells with the preservation number CGMCC No. 14700. After injection, ascites were collected and purified, then the monoclonal antibody was preserved at low temperature.

In another embodiment, BALB/c mice with 8 to 10 weeks, were intraperitoneally injected with paraffin oil 1 mL each. After 7 days, each mouse intraperitoneally is injected with 1×106 hybrid tumor cells with the preservation number CGMCC No. 14700.

From 7 days start collecting ascites, purified by bitter-ammonium sulfate law, the monoclonal antibody was preserved at −20° C.

The present invention provides an application of meroxicam monoclonal antibody, which can be applied to specifically identify meroxicam.

The present invention provides a detection kit for the preparation of either the above hybrid tumor cell line secreting meloxicam monoclonal antibody or the above meroxicam hapten or the above meroxicam complete antigen or the above meroxicam coated original or the above meroxicam monoclonal antibody.

The advantages of the invention are:
1. The monoclonal antibody cell line obtained by the invention has a good detection sensitivity and specificity for meloxicam (IC50 value is 0.1 ng/ml).
2. The invention provides a new synthetic method of meroxicam hapten, complete antigen and coating antigen.
3. The monoclonal antibody cell line obtained by the invention can be used for immunoassay detection.

Preserve Biological Materials

A hybrid tumor cell line that secretes monoclonal antibodies to meroxicam, which the classification is called monoclonal cell lines, has been deposited with the general microbiological center of China General Microbiological Culture Collection Center (No. 3, Yard 1, Beichen Road, Chaoyang District, Beijing, China) under Accession Number CGMCC No. 14700 on Dec. 5, 2017.

DESCRIPTION OF PREFERRED EMBODIMENTS

Figure 1:
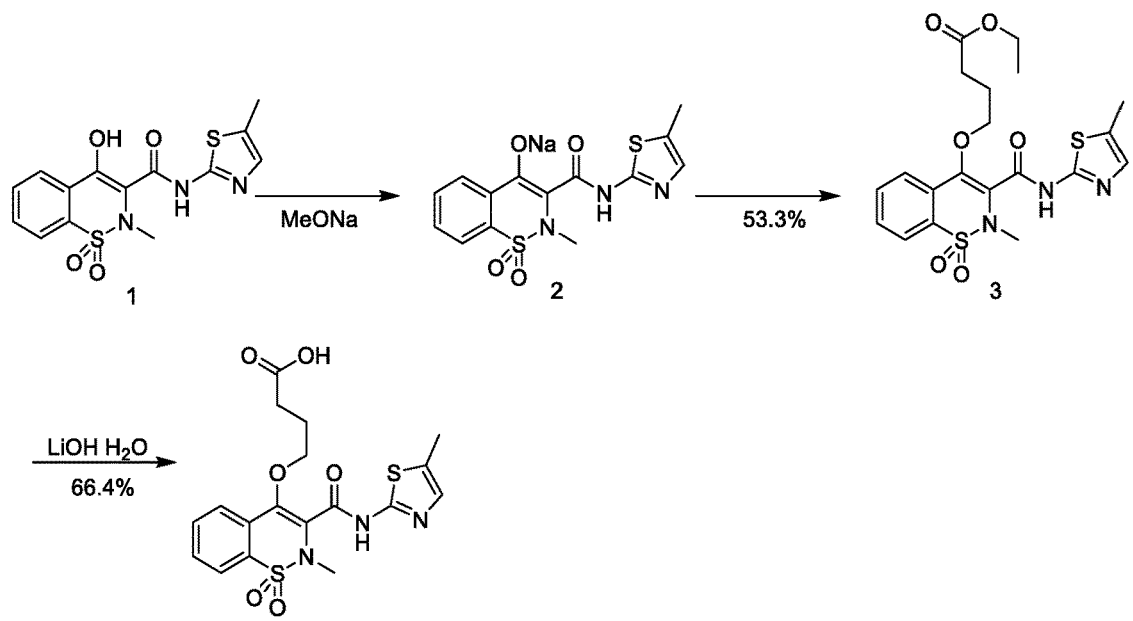
FIG. 1 shows the synthetic process of meroxicam haptens.

The detailed implementation of the invention is further described as follows. The following embodiments are used to illustrate the invention, but not to limit the scope of the invention.

The media involved in the following embodiments are as follows:

RPMI-1640 medium: Fetal bovine serum 10%, 1-arginine 290 mg/L, calcium nitrate 100 mg/L, 1-asparagine 50 mg/L, anhydrous sulfate magnesium 488 mg/L, L-asparagine 20 mg/L, potassium chloride 400 mg/L, L-glutamic acid 20 mg/L, sodium chloride 6000 mg/L, glycine 10 mg/L, glucose 2000 mg/L, L-histidine 15 mg/L, reduced glutathione 1 mg/L, L-hydroxyproline 20 mg/L, phenol red 5 mg/L, L-isoleucine 50 mg/L, L-glutamine 50 mg/L, biotin 50 mg/L, L-lysine hydrochloride 40 mg/L, D-pantothenic acid 15 mg/L, L-threonine 20 mg/L, pyridrol hydrochloride 1 mg/L, L-tryptophan 5 mg/L, riboflavin 0.2 mg/L, L-tyrosine 23.19 mg/L, thiamine hydrochloride 1 mg/L, L-valine 20 mg/L, vitamin B12 0.005 mg/L, para aminobenzoic acid 1 mg/L.

The reagents involved in the following embodiments are as follows:

Carbonate buffer solution (CBS): Weigh Na2CO3 1.59 g and NaHCO$_3$ 1.59 g, then mixture with steaming water, plus double steamed water to 800 mL, adjust pH value to 9.6, Add double steaming water for constant volume (1000 mL), state for 4 V;

Phosphate Buffer solution (PBS): 8.00 g NaCl, 0.2 g KCl, 0.2 g KH2PO4, 2.9 g Na2HPO4.12 H2O, dissolved in 800 mL pure water, pH was adjusted to 7.2~7.4 with NaOH or HCl, then the capacity was constant to 1000 mL;

PBST: Add 0.5 ml Tween-20 to 1000 mL PBS solution (0.01 mol/L, pH 7.4);

Antibody Diluent: Washing buffer containing 0.1% gelatin;

TMB Substrate: Mixture of solution A and solution B with 1:5;

Solution A: Na2HPO4.12H2O 18.43 g, citric acid 9.33 g, constant to 1000 mL with pure water. Solution B: 60 mg TMB dissolved in 100 mL ethylene glycol.

The test methods involved in the following embodiments are as follows:

Test method for the yield of meroxicam hapten: the ratio of the quality of the final product after purification to that of the raw material.

Melo standard product inhibition test method:

Indirect competitive enzyme-linked immunosorbent assays (ic-ELISA): The synthetic coating antigen were used to sheathe. Mouse serum was diluted with antibody dilutions of 1000, 3000, 9000 and 27000 times, and the standard product solution was prepared. The above four rows of the enzyme label plate were added with 50 mm L/hole in PBS, and the next four rows with 50 mm L/hole in the standard solution, and then the mice serum of different concentrations were added with 50 mm L/hole at 37° C. for 30 min incubation, adding enzyme mark after two resistance. After color development and termination, OD450 nm are measured. The inhibition rate is calculated according to the absorbance value, inhibition rate=the OD value of the hole with the inhibitor/OD value of the control hole without the inhibitor.

Example 1

Synthesis of Meroxicam Hapten

The synthesis path is shown in FIG. 1.

1 g of compound 1 was dissolved in 50 ml of methanol solution, and stirred at 157° C. for the night after adding 157 mg MeONa, and then the compound 1 was gotten. 1.20 g of compound 2 was dissolved 30 ml DMF, and added 1.20 mg Ethyl 4-bromobutyrate stir at 80° C. for the night, and then the mixture 2 was gotten. The step 4 is to concentrate the obtained mixture 2 and then purify it with a silica gel column to obtain compound 3. The 800 mg compound 3 was dissolved into 3 mL tetrahydrofuran and 1 mL water, adding 180 mg 1-hydrated lithium hydroxide, adjusting pH to 4-6, and stirring at room temperature overnight to get mixture 4. The aqueous solution layer with ethylamine from mixture 4 was extracted, and the organic layer was combined, washing with salt water, drying with anhydrous sodium sulfate and being concentrated to obtain meloxicam hapten.

The products of compound 3 and haptens are calculated.

Compound 3 production rate of 53.3%, the yield of the hapten was 66.4%.

Example 2

Complete Antigen Synthesis of Meloxicam 1.7 mg Melo, 2.2 mg 1-ethyl carbodiimide hydrochloride and 1.4 mg N-hydroxysuccinylimide was dissolved into 400 phenyl-anhydrous N, N-dimethylamine, stirring 6-8 h at room temperature to obtain A1 solution. 10 mg keyhole blood blue protein (KLH) (Melo to KLH Moore ratio of 1500:1) was diluted with an appropriate amount of boric acid buffer solution, and B1 solution was obtained. At room temperature, A1 solution was added to B1 solution one drop at a time. Complete antigen (Melo-KLH) is obtained by separating complete antigen and uncoupled small molecule hapten (Melo) by dialysis.

1.7 mg Melo, 2.2 mg 1-ethyl carbodiimide hydrochloride and 1.4 mg N-hydroxysuccinylimide was dissolved into 400 phenyl-anhydrous N, N-dimethylamine, stirring 6-8 h at room temperature to obtain A1 solution. 10 mg keyhole blood blue protein (KLH) (Melo to KLH Moore ratio of 3000:1) was diluted with an appropriate amount of boric acid buffer solution, and B1 solution was obtained. At room temperature, A1 solution was added to B1 solution one drop at a time. Complete antigen (Melo-KLH) is obtained by separating complete antigen and uncoupled small molecule hapten (Melo) by dialysis.

1.7 mg Melo, 2.2 mg 1-ethyl carbodiimide and 1.4 mg N-hydroxysuccinylimide was dissolved into 400 phenyl-anhydrous N, N-dimethylamine, stirring 6-8 h at room temperature to obtain A1 solution. 10 mg keyhole blood blue protein (KLH) (Melo to KLH Moore ratio of 4500:1) was diluted with an appropriate amount of boric acid buffer solution, and B1 solution was obtained. At room temperature, A1 solution was added to B1 solution one drop at a time. Complete antigen (Melo-KLH) is obtained by separating complete antigen and uncoupled small molecule hapten (Melo) by dialysis.

Example 3

Synthesis of the Meroxicam Coating Antigen 1.8 mg Melo 2.4 mg 1-ethylenediamine hydrochloride salt 1.45 mg N-hydroxysuccinylimide was dissolved into 300 phenyl-anhydrous N, N-dimethylamine, and stir it 6-8 h at room temperature to obtain A2 solution. 5 mg of chicken egg albumin (OVA) was dissolved in 2 mL boric acid buffer solution to obtain B2 solution. At room temperature, A2 solution was added to B2 solution, and mixed solution was obtained after overnight reaction at room temperature. Complete antigens, uncoupled small molecule haptens (Melo) and coating antigen (Melo-OVA) were separated by dialysis.

Example 4

Preparation of Hybrid Tumor Cell Lines that Secrete the Monoclonal Antibody of Meloxicam Animal Immunization Healthy Balb/C mice aged 6-8 weeks were selected for immunization. BALB/c mice were immunized by subcutaneous injection of three different molar ratios of Melo complete antigen and equivalent freund's adjuvant. For the first immunization, 100 ug of each mouse was injected with complete freund's adjuvant, after which the whole freund's adjuvant was used. Each mouse was injected with 50 ug between the first immunization and the second booster immunization for 28 days, and between multiple booster immunization for 21 days, and blood was collected for 7 days after the third immunization (5 ul Tail blood of mice+995 ul antibody diluent=antiserum). The serum titer and inhibition of mice were determined by ic-elisa, and the mice with high titer and good inhibition were selected for the sprint immune after the fourth immunization session by intraperitoneal injection with the dosage halved and without any adjuvant.

The serum titer and inhibition rate of mice were measured by IC-ELISA. It was found that when the anti-serum dilution multiple was 3K and the concentration of coating antigen was 0.1 μg/mL, the potency of the mice immunized was 71%, 52% and 51 after the addition of 50 ppb Melo standard with immunogen Melo-KLH 1500:1, Melo-KLH 3000:1 and Melo-KLH 4500:1 were 1.648, 1.333 and 1.613 respectively.

Obviously, the titer and inhibition rate of immunized mice with immunogen melo-klh 1500:1 were the highest, so this mouse was selected for the next experiment.

Cell Fusion

After 3 days of shock immunity, cell fusion was performed by PEG (polyethylene glycol, with a molecular weight of 1500). The steps are as follows:

After mice were killed by cervical dislocation, the their eyeball blood was picked and soaked immediately in 75% alcohol disinfection about 5 min. The spleen of the mice was taken out by aseptic operating, grinded moderately by the glue head of the syringe and gotten the splenocyte suspension through 200 mesh cell screen. And the splenocyte suspension was collected and centrifuged (1200 RPM, 8 min). And then washing spleen cells three times with RPMI-1640 medium, after the last time the centrifugal, spleen cells were diluted to a certain volume, count, and standby application.

Collect sp2/0 cells: Sp2/0 tumor cells were cultured in 5% CO2 culture box with RPMI-1640 medium containing 10% FBS (fetal bovine serum) between 7 and 10 days before fusion. Before fusion, the number of sp2/0 tumor cells was required to reach 1-4×107, ensuring that sp2/0 tumor cells were in the logarithmic growth stage. At the time of fusion, tumor cells were collected and suspended in rpm-1640 basic medium for cell counting.

The fusion process lasted for 7 min. During the first min. 1 mL of PEG1500 was added to the cells from slow to fast. For the second minute, there was stewing. For the three and four minutes, culture medium of 1 ml RPMI-1640 was added within 1 min. For the five and six minutes, Culture medium of 2 m RPMI-1640 was added within 1 min. For the seven minute, 1 mL rpm-1640 culture medium was added every 10 s. Then the cells were under warm bath at 37° C. 5 min, abandoned supernatant through centrifugation (800 rpm, 8 min), resuspended with 20% fetal bovine serum. And then 2% of the 50×HAT RPMI-1640 filter medium added to 96 hole cell plate according to the 200 μL/hole, at 37° C. and 5% CO2 incubator to cultivate.

Cell Screening and Cell Line Establishment

On the third day of cell fusion, the fusion cells were partially replaced with the rpm-1640 screening medium, and on the fifth day, the cells were fully replaced with the rpm-1640 transition medium containing 20% fetal bovine serum and 1% 100×HT, and the supernatant was taken on the seventh day for screening.

Screening is divided into two steps: the first step was to screen out the positive cells by indirect ELISA; in the second step, Melo was selected as the standard product, and the inhibitory effect of positive cells was measured by indirect competitive ELISA. Cell pores that had good inhibition on all meroxicam standard products were selected, and subclone was conducted by finite dilution method. The same method was used for detection, and the cell lines were obtained after repeated for three times.

Example 5

Preparation of Meloxicam Monoclonal Antibody

BALB/c mice with 8 to 10 weeks, were intraperitoneally injected with paraffin oil 1 mL each. After 7 days, each mouse intraperitoneally is injected with 1×106 hybrid tumor cells secreting meroxicam monoclonal antibody. From 7 days start collecting ascites, purified by bitter-ammonium sulfate law, in the condition of partial acid; n-caprylic acid can precipitate other heterologous proteins except IgG immunoglobulin in ascites, and then the precipitation was discarded after centrifuge. The monoclonal antibody of IgG type was precipitated with ammonium sulfate solution of equal saturation, and then the supernatant was discarded after centrifuge. After dissolving precipitate with 0.01 MPBS solution (pH7.4), being desalination through dialysis, finally, the monoclonal antibody was obtained after purification and preserved at −20° C.

Example 6

Identification of Meroxicam Monoclonal Antibody coating: coating antigen Melo-OVA had reacted for 2 h after serial dilution of the pH of 9.6 of 0.05 m carbonate buffer from 1 μg/mL, 100 μL/hole at 37° C.

Washing: the solution in the plate was poured out and wash it 3 times with wash solution, 3 min each.

Sealing: After pat dry, 200 μL/hole sealing fluid was added to reaction within 2 h at 37° C., drying after washing.

Sample adding: Antiserum (After the blood was collected from the tail of the mice, the antiserum was diluted with antibody diluent) was diluted from the ratio of 1:1000, and was added into the degree of the dilution of coating hole, 100 μL/hole, and had reacted at 70° C. for 30 min. After fully washing, HRP—Goat anti Mouse IgG that had diluted with the ratio of 1:3000 was added and reacted at 37° C. for 30 min, 100 μL/hole;

Coloration: The enzyme label plate was taken out, after washing, each hole was added into TMB Color liquid, and reacted at 37° C. for 15 min avoiding light.

Termination and determination: To terminate the reaction, 50 μL termination solution was added to each hole, and then the value of OD450 of each hole was measured with an enzyme marker.

Figure 2:
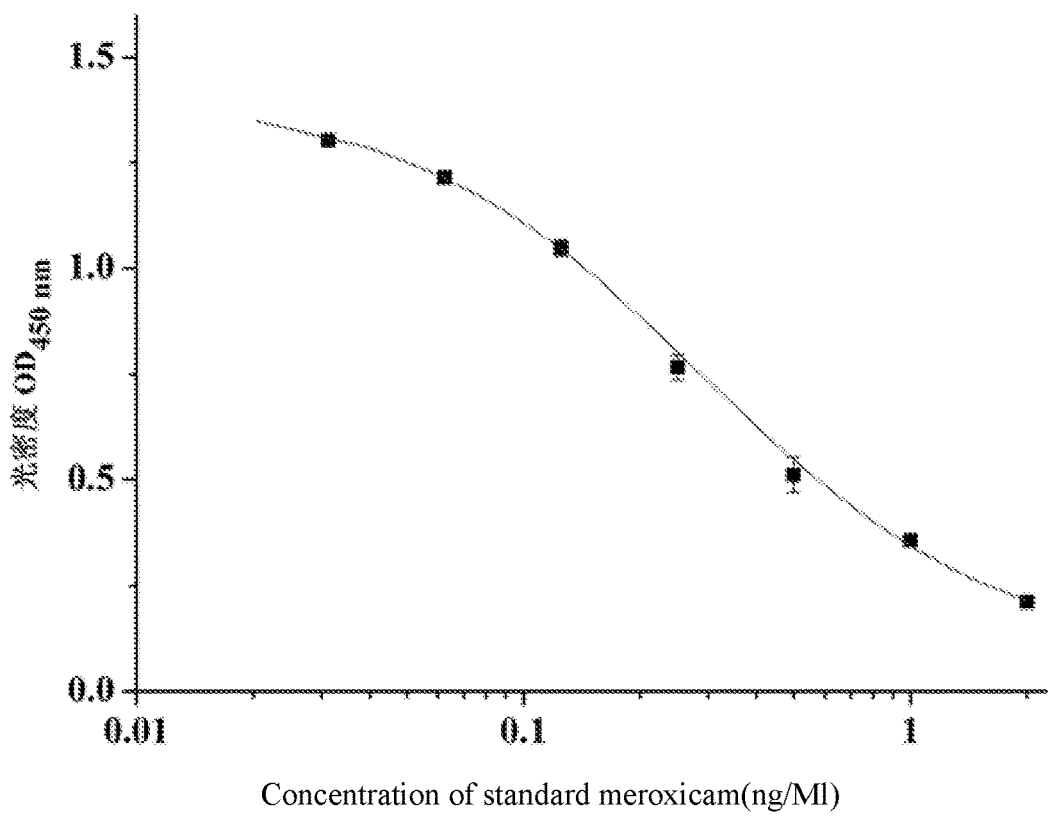
FIG. 2 shows the standard curve of inhibition of meloxicam by meroxicam monoclonal antibody.

The IC50 of the monoclonal antibody Melo was 0.3 ng/mL and the minimum detection limit was 0.1 ng/mL detected by ic-ELISA, indicating a good sensitivity to Melo and can be used for Melo immunoassay. (the standard curve of inhibition of meloxicam by meroxicam monoclonal antibody was shown in FIG. 2).

The above description is only a preferred method of implementation of the invention, and is not used to limit the invention. It should be noted that, for ordinary technical personnel in the field of technology, some improvements and variations can be made under the technical principles of the invention. These improvements and variations should also be considered as the scope of protection of the invention.

What is claimed is:

1. A hybridoma cell line of secreting meloxicam monoclonal antibodies deposited with the general microbiological center of China General Microbiological Culture Collection Center (No. 3, Yard 1, West Beichen Road, Chaoyang District, Beijing, China) under Accession Number CGMCC No. 14700 on Dec. 5, 2017.

2. A meroxicam monoclonal antibody obtained from the hybrid tumor cell line of claim 1.

* * * * *